US008591502B2

(12) United States Patent
Vogler

(10) Patent No.: US 8,591,502 B2
(45) Date of Patent: Nov. 26, 2013

(54) LASER SYSTEM FOR REFRACTIVE SURGERY

(75) Inventor: Klaus Vogler, Eckental (DE)

(73) Assignee: Wavelight AG, Erlangen (DE)

( * ) Notice: Subject to any disclaimer, the term of this patent is extended or adjusted under 35 U.S.C. 154(b) by 1587 days.

(21) Appl. No.: 11/835,283

(22) Filed: Aug. 7, 2007

(65) Prior Publication Data

US 2008/0058780 A1 Mar. 6, 2008

(30) Foreign Application Priority Data

Aug. 7, 2006 (EP) ................................... 06016465

(51) Int. Cl.
*A61F 9/008* (2006.01)

(52) U.S. Cl.
USPC ............................................................. 606/5

(58) Field of Classification Search
None
See application file for complete search history.

(56) References Cited

U.S. PATENT DOCUMENTS

| 6,755,819 B1 * | 6/2004 | Waelti ................................ 606/5 |
| 2003/0110862 A1 * | 6/2003 | Lubatschowski et al. ...... 73/644 |
| 2004/0102765 A1 * | 5/2004 | Koenig ............................. 606/5 |

FOREIGN PATENT DOCUMENTS

| DE | 10020559 | 10/2001 |
| WO | 02/076355 | 10/2002 |
| WO | 2004/061425 | 7/2004 |

OTHER PUBLICATIONS

Fujimoto et al., "Optical Coherence Tomography" in Ultrafast Lasers, Technology and Applications. Edited by Martin E. Fermann, Almantas Galvanauskas, and Gregg Sucha (CRC Press 2002).*
Rainer Bohm et al., "Das Spectrum einer LED and die Leistung einer Laserdiode", Laser & Photonic, May 2005, pp. 28-31.
Lynn M. Savage, "Adaptive optics improves OCT-based retinal imaging", Biophotonics International, Dec. 2005, pp. 48, 49.
Pei-Lin Hsiung et al., "Optical Coherence Tomography", Biophotonics International, Sep. 2003, pp. 36-40.
Rainer Bohm et al., "Das Spectrum einer LED und die Leistung einer Laserdiode", Laser & Photonic, May 2005, pp. 28-31.
Holger Lubatschowski et al., "Application of ultrashort laser pulses for intrastromal refractive surgery", Graefe's Archive for Clinical and Experimental Ophthalmology, Jan. 2000, pp. 33-39.
Wolfgang Drexler, "Ultrahigh-resolution optical coherence tomography", Journal of Biomedical Optics, Volume No. 1, Jan./Feb. 2004), pp. 47-74.
Jan Posthumus, "Modelocked fibre lasers aid short pulse creation", Optics Org., OLE Product Guide 2006.
FemtoFiber Scientific Brouchure, "FemtoFiber Lasers: Mode of Operation".
EP 06 01 6465 European Search Report, Jan. 15, 2007.

* cited by examiner

*Primary Examiner* — Sam Yao
*Assistant Examiner* — Scott T Luan
(74) *Attorney, Agent, or Firm* — Haynes and Boone, LLP

(57) ABSTRACT

A laser system for refractive surgery comprises a laser beam for generating laser beam pulses and optical means for directing these laser beam pulses as a working beam onto an eye. Some of the working radiation is extracted for optical coherence tomography, in order to measure geometrical structures in the cornea.

17 Claims, 1 Drawing Sheet

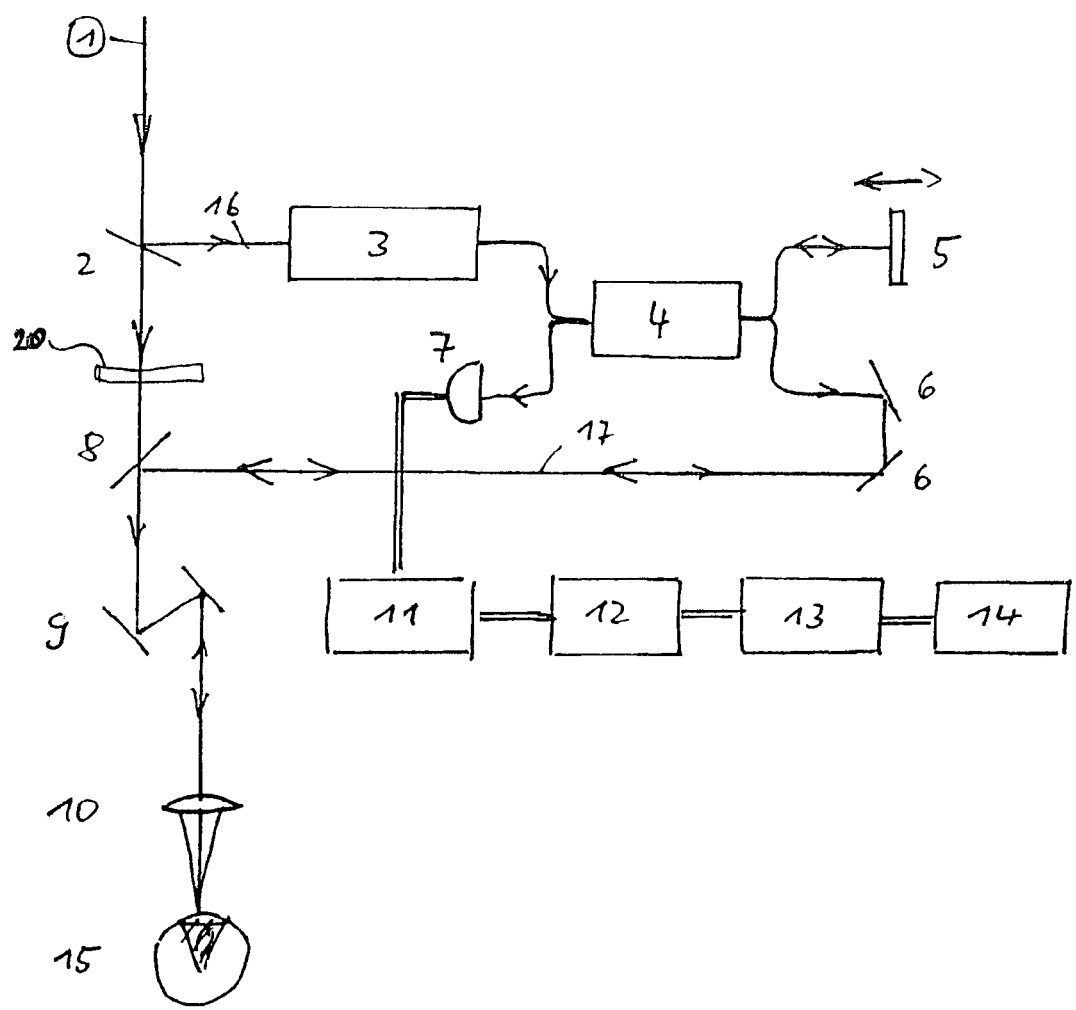

LASER SYSTEM FOR REFRACTIVE SURGERY

PRIORITY

This patent application claims priority to European Patent Application No. 06 016 465.4 filed Aug. 7, 2006, the entirety of which is incorporated by reference herein.

BACKGROUND

The invention relates to a laser system for refractive surgery, having a laser beam source for generating laser beam pulses and having optical means for directing laser beam pulses as a working beam onto or into an eye.

In opthalmology, the term "refractive surgery" with lasers describes the interaction of laser radiation with parts of the eye in order to modify the refractive properties of the eye and therefore its imaging properties, so as to eliminate or at least alleviate imaging defects.

One particularly important example of refractive surgery is the correction of an eye's defective vision by the LASIK technique. In LASIK according to the prior art, the cornea is first cut laterally by means of a microkeratome and the resulting so-called flap is folded to the side. In the cornea's stroma thus exposed, so-called ablation is carried out with laser radiation i.e. tissue is removed according to a so-called ablation profile. The flap is then folded back and a relatively painless and rapid healing process takes place. After this intervention, the cornea has different imaging properties and the defective vision is remedied or reduced.

The above-described lateral incision into the cornea is conventionally carried out in the prior art with a so-called microkeratome, i.e. an oscillating mechanical blade. So-called femtosecond microkeratomes have recently also been used, in which case femtosecond laser pulses are focused into the tissue of the cornea so as to generate so-called laser-induced photodisruptions there in the corneal tissue by closely neighboring focal points of the radiation, which are guided over the corneal tissue so that a cut is finally obtained as in the case of a mechanical microkeratome.

The present invention will be explained in more detail below with reference to the LASIK technique as outlined above. Very generally, however, the laser system according to the invention is also suitable for other refractive surgery methods.

Optical coherence tomography (OCT) has recently gained acceptance as a diagnostic method in opthalmology. OCT has for instance been used for measurements on the retina in vivo, see Lynn M. Savage: "Adaptive optics improves OCT-based retinal imaging" in Biophotonics International, December 2005, 48-49. Owing to axial layer resolution in depth, the measurements carried out by this technique on the retina in vivo deliver images which provide information about disease patterns of the retina before they can actually be seen on the retinal surface, for example using the conventional split lamp technique.

Another application of OCT in refractive surgery is disclosed by U.S. Pat. No. 6,755,319 B1. In this case, photoablation of the cornea is accompanied by an OCT measurement method, in order to measure and therefore monitor the thickness of the cornea during the intervention. Different radiation sources are provided there for the so-called working beam on the one hand, i.e. the laser beam which carries out the refractive surgery, and the measurement beam for the OCT method on the other hand.

Further fundamentals and applications of OCT can be found for example in P. Hsiung, T. H. K O, S. Bourquin, A. Aguirre, P. Herz and J. Fujimoto, "Optical Coherence Tomography", in Biophotonics International, September 2003, 36-40.

SUMMARY

It is an object of the invention to provide a laser system for refractive surgery, which permits optical coherence tomography by comparatively simple means before, during or after the refractive intervention.

To this end the invention provides a laser system for refractive surgery having a beam source for generating laser beam pulses and optical means for directing the laser beam pulses onto or into an eye, wherein some of the generated laser pulses are diverted by means of at least one of the optical means as a measurement beam into a device for optical coherence tomography.

According to the invention, an additional OCT measurement beam source further to the working beam source can thus be obviated.

A preferred configuration of the invention provides means for increasing the spectral bandwidth of the laser beam pulses diverted for the measurement. If a femtosecond laser is used as a common source for the working beam and the measurement beam, then this laser may for example be used for the above-described LASIK cutting in the cornea while the measurement beam for the optical coherence tomography is diverted via a beam splitter. OCT requires a measurement beam with as large a spectral bandwidth as possible. The spectral bandwidth of the measurement beam determines the axial resolving power of the OCT according to the Wiener-Khinchin theorem (R. Böhm and E. Overbeck "Das Spectrum eines LED und die Leistung einer Laserdiode, OCT-Untersuchung von dünnen Schichten" in Laser & Photonic May 2005, 28-31). The inventive spectral increase of the bandwidth of the diverted measurement beam therefore produces a femtosecond continuum which makes it possible to generate a spectrally very broadband emission, for example in a single-mode fibre. With bandwidths in excess of 400 nm and particularly in excess of 800 nm, depth resolutions better than 1 µm are achieved. The axial depth resolving power describes the resolution of the measurement in the direction of the laser beam, i.e. in the depth of the tissue being studied.

Another configuration of the invention provides means for representing data obtained by the optical coherence tomography, for example images, during the refractive surgery so that the doctor is provided with information about the current state of the operative result during the process.

The invention is particularly suitable for cutting the above-explained flap during LASIK. If the above-described high axial resolutions in the range of 1 µm are achieved, then the quality of the LASIK cutting can therefore also be monitored and, in particular, roughnesses due to the photodisruptions can also be monitored i.e. the smoothness of the cutting can be monitored.

By these measures, the invention achieves a high resolving power during the measurement without a separate (and expensive) OCT measurement beam source.

A variant of the invention provides a selectively actuable shutter in the beam path of the working beam so that OCT can be carried out independently of any laser treatment, for example before or after the LASIK cutting.

BRIEF DESCRIPTION OF THE DRAWING

FIG. 1 is an exemplary embodiment of the invention which will be explained in more detail below with the aid of the drawing.

DETAILED DESCRIPTION

The single FIG. 1 schematically shows a laser system for refractive surgery, having integrated optical coherence tomography (OCT).

The exemplary embodiment relates to a femtosecond laser system as a microkeratome, for the purpose of carrying out measurements in the cornea in real-time (on-line) when cutting a flap, i.e. in particular measurements concerning the geometrical profile of the cutting and/or the roughness of the cutting. The dimensions of the flap and of the remaining corneal tissue may also be measured (pachymetry).

In a manner known per se, a laser beam source delivers laser beam pulses 1 with a wavelength of 1035 nm ($\lambda 1$), a pulse length of 400 fs, from 5 to 10 µJ of energy, and a repetition rate of 200 kHz. These laser beam pulses 1 are used in a manner known per se for the above-described production of a LASIK flap. These laser beam pulses are referred to here as the working beam. The working beam is directed in a manner known per se via a scanner 9 and a focusing lens onto the patient's eye 15. In the tissue of the cornea, the focused radiation generates the described photodisruptions and the cut is made in the tissue out by placing the individual focal points of the pulses very close together. The focal points are thus placed in an x-y plane so that a foldable flap is produced.

According to the invention, measurement pulses 16 are diverted by a beam splitter 2 from the laser pulses 1. A beam splitter 2 extracts from 5 to 10% of the incident radiation into the measurement beam 16.

Means 3 for generating a femtosecond continuum with the wavelength $\lambda 2$ are arranged in the measurement beam 16. As explained above, the resolving power of an OCT measurement increases with the spectral bandwidth of the measurement beam. The means 3 thus generate a femtosecond continuum having a very broadband emission with wavelengths in excess of 400 nm. Bandwidths of from more than 400 nm up to 800 nm can currently be achieved with single-mode fibers (cf. J. Posthumus, "Modelocked Fibre Lasers Aid Short Pulse Creation", in Optics. Org, OLE Product Guide 2006). Single-mode fibers are also described in the data sheet Integral OCT from FEMTOLASERS Produktion GmbH.

The means 3 thus generate broadband radiation around a wavelength of 1035 nm, with a pulse length of 400 fs and a pulse energy of 1 µJ, as well as a bandwidth (FWHM) of from 400 to 800 nm. This provides an axial depth resolving power better than 1 µm for the OCT described below.

The components denoted by 3,4, 5,6 and 7 in the FIGURE form an OCT measurement system known per se comprising a fibre-optic beam splitter 4, and mobile mirror 5, deflection mirrors 6 for the measurement branch and a photodetector 7. The arrangement corresponds to Michelson interferometer. The mirror 5 is mobile, and the detector 7 measures constructive or destructive interferences depending on the optical wavelength to which the reference mirror 5 is set.

Via the deflection mirrors, the broadband OCT measurement beam 17 is steered onto a dichroic mirror 8 which spatially superimposes the OCT measurement beam 17 exactly on the working beam. Just like the working beam, the OCT measurement beam 17 is therefore also directed by the scanner 9 and the focusing lens 10 into the patient's eye 15. OCT measurement radiation reflected in the depth layers of the specimen (here the eye 15) travels via the dichroic mirror 8 back into the OCT measurement arrangement, and the said constructive or destructive interferences are measured at the detector 7 depending on the setting of the mirror 5. The output signal of the photodetector 7 travels via an amplifier 11 into a bandpass filter 12 and then into a computer 13 for carrying out a fast Fourier analysis known per se for the OCT measurement. The representation thus generated on a monitor 14 provides not only a depth profile of the cornea, in which the cutting plane generated by the femtosecond working beam can be seen, but also, given sufficient spatial coherence and wavefront quality, a depth profile which is resolved laterally in a transverse direction (z direction) and is therefore three-dimensional, owing to the deflection (of the scan) together with the working beam by means of the scanner 9.

The diverted measurement beam 16 may have a higher repetition rate and a significantly lower pulse energy, i.e. very much less than 1 µJ, than the refractively effective more energetic working beam, for example the pulse repetition rate of the fs oscillator (a pulse repetition rate of 1 MHz or more), while the refractively effective working beam has a pulse repetition rate of 200 kHz with a pulse energy of more than 5 µJ. The disturbance to the refractively effective working beam by the measurement beam is therefore negligible. With the parameters of the measurement beam, so-called self-phase modulation in a single-mode fibre with a diameter of from 5 to 10 µm is readily possible. If a higher repetition rate is provided for the measurement beam 16 than for the refractive working beam, then the extraction of the measurement beam preferably takes place in the femtosecond laser system itself, for example between the oscillator and the amplifier there.

The diverted measurement beam may also be used independently of the working beam, for example before or after the LASIK cutting, by blocking the working beam with a shutter (or a so-called beam dump) 20.

The described measurement method makes it possible to identify roughness of the flap cutting in LASIK, which may readily lie in the range of several µm. The geometrical proportions of the edge surfaces of the cornea as well as in the cornea can be resolved, i.e. in particular the cutting depth and also the edge cut may be measured. Besides the roughness of the flap bed, it is also possible to identify the edge cut, for example the inclination angle.

The invention claimed is:

1. Laser system for refractive surgery, having a laser beam source configured to generate laser beam pulses and having optical means for spatially separating each of the generated laser beam pulses into a working beam and a measurement beam and for directing the working beam and the measurement beam coaxially onto or into an eye, wherein the measurement beam is also directed into a device for optical coherence tomography.

2. Laser system according to claim 1, having means for increasing the spectral bandwidth of a separated portion of each of the generated laser beam pulses to define the measurement beam.

3. Laser system according to claim 1, characterized in that the optical means are designed for LASIK cutting.

4. Laser system according to claim 3, characterized in that the laser beam source emits femtosecond laser pulses.

5. Laser system according to claim 1, characterized in that the optical means are designed for corneal ablation.

6. Laser system according to claim 1, having means for representing data obtained by the optical coherence tomography during the refractive surgery.

7. Laser system according to claim 1, having a selectively actuable shutter in the beam path of the work beam.

8. A system for eye surgery, comprising:
a laser beam source configured to generate at least one laser beam pulse;
a beam splitter configured to spatially divide said laser beam pulse into a working beam for tissue ablation and a measurement beam;
means for receiving said measurement beam and generating an optical coherence tomography measurement beam;
a scanner receiving both the working beam and the measurement beam, wherein the scanner is operable to direct both beams into the eye;
a photodetector configured to receive at least a portion of a reflected measurement beam traveling from the eye; and
a processor for comparing the measurement beam to the reflected measurement beam to determine the optical coherence tomography measurement for the tissue ablation of the eye.

9. The system of claim 8, further comprising an optical system in communication with the laser beam source, the optical system configured to focus the working beam for LASIK cutting.

10. The system of claim 9, wherein the laser beam source emits femtosecond laser beam pulses.

11. The system of claim 8, wherein the working beam is configured for corneal tissue ablation.

12. The system of claim 8, further comprising a selectively actuable shutter in the beam path of the work beam, the shutter configured to selectively block transmission of the working beam.

13. The system of claim 8, wherein the means for receiving said measurement beam and generating the optical coherence tomography measurement beam is configured to generate a femtosecond continuum in the measurement beam.

14. The system of claim 13, wherein the femtosecond continuum has a bandwidth between about 400 nm and about 800 nm.

15. The system of claim 8, wherein the beam splitter divides between 5% and 10% of the laser beam pulse into the measurement beam.

16. The system of claim 15, wherein the measurement beam has a repetition rate greater than the working beam.

17. The system of claim 16, wherein the measurement beam has a pulse energy less than the working beam.

* * * * *